(12) United States Patent
Lei et al.

(10) Patent No.: US 10,793,586 B2
(45) Date of Patent: Oct. 6, 2020

(54) QUATERNARY AMMONIUM ETIDRONATES

(71) Applicant: INNOVATIVE WATER CARE, LLC, Alpharetta, GA (US)

(72) Inventors: Deqing Lei, Alpharetta, GA (US); Nidhi Rawat, Alpharetta, GA (US); Amber Khanzada, Alpharetta, GA (US)

(73) Assignee: INNOVATIVE WATER CARE, LLC, Alpharetta, GA (US)

( * ) Notice: Subject to any disclaimer, the term of this patent is extended or adjusted under 35 U.S.C. 154(b) by 7 days.

(21) Appl. No.: 16/151,958

(22) Filed: Oct. 4, 2018

(65) Prior Publication Data

US 2019/0106445 A1    Apr. 11, 2019

Related U.S. Application Data

(60) Provisional application No. 62/568,595, filed on Oct. 5, 2017.

(51) Int. Cl.
   *C07F 9/54*     (2006.01)
   *A01N 57/20*    (2006.01)
   (Continued)

(52) U.S. Cl.
   CPC .......... *C07F 9/5449* (2013.01); *A01N 33/12* (2013.01); *A01N 57/20* (2013.01); *C02F 1/50* (2013.01);
   (Continued)

(58) Field of Classification Search
   CPC ...... C07F 9/5449; C07F 9/386; C07C 211/63; A01N 33/12; A01N 57/20; C02F 1/722;
   (Continued)

(56) References Cited

U.S. PATENT DOCUMENTS 6,399,827 B1    6/2002  Hahn et al.
2001/0037531 A1   11/2001  Lorenz
(Continued)

FOREIGN PATENT DOCUMENTS

JP        09077610        3/1997
WO    WO 2009/038919 A1    3/2009

OTHER PUBLICATIONS

Demadis et al., "Controlled Release of Bis(phosphonate) Pharmaceuticals from Cationic Biodegradable Polymeric Matrices", I&EC Research, 2011, vol. 50, Issue 9, pp. 5873-5876.
(Continued)

*Primary Examiner* — Taiwo Oladapo
(74) *Attorney, Agent, or Firm* — Brown Rudnick LLP

(57) ABSTRACT

The present invention provides a quaternary ammonium etidronate compound (QAE) comprising a quaternary ammonium cation and an etidronate anion, having the Formula I.

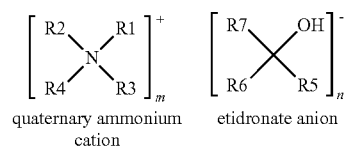

A method for the preparation of such compounds is described by reacting a quaternary ammonium salt with an etidronic acid or salt thereof. Variable ratios of each reactant may also be used to form different QAE compounds. The quaternary ammonium etidronate compounds is useful in water treatment, cosmetic, hygiene, personal care, paint,
(Continued)

coating, wood treatment, agrochemical, antimicrobial, disinfectant, or biocidal compositions; as the compound provides high anti-corrosive and biocidal properties; and low scaling properties. A water treatment composition is also described, having a QAE compound of Formula I and a water treating biocidal agent, useful in cooling towers and other recirculating water, or recreational water system.

24 Claims, 1 Drawing Sheet

(51) Int. Cl.

| | |
|---|---|
| *C02F 1/50* | (2006.01) |
| *C07C 211/63* | (2006.01) |
| *A01N 33/12* | (2006.01) |
| *C07F 9/38* | (2006.01) |
| *C02F 1/72* | (2006.01) |
| *C02F 1/76* | (2006.01) |
| *C02F 103/00* | (2006.01) |
| *C02F 103/42* | (2006.01) |
| *C02F 101/34* | (2006.01) |

(52) U.S. Cl.
CPC .............. *C02F 1/722* (2013.01); *C02F 1/76* (2013.01); *C07C 211/63* (2013.01); *C07F 9/386* (2013.01); *C02F 2101/34* (2013.01); *C02F 2103/007* (2013.01); *C02F 2103/42* (2013.01); *C02F 2303/04* (2013.01)

(58) Field of Classification Search
CPC .......... C02F 1/76; C02F 1/50; C02F 2101/34; C02F 2103/007; C02F 2303/04; C02F 2103/42
See application file for complete search history.

(56) References Cited

U.S. PATENT DOCUMENTS

| | | | |
|---|---|---|---|
| 2002/0028754 A1* | 3/2002 | Johansen | ............... A01N 37/46 510/302 |
| 2011/0015120 A1* | 1/2011 | Bortolin | ............... A61K 8/4926 514/3.3 |
| 2012/0157579 A1* | 6/2012 | Parent | ...................... C08F 8/30 524/35 |
| 2013/0136803 A1 | 5/2013 | Unhoch et al. | |
| 2016/0066571 A1* | 3/2016 | Lei | ......................... A01N 33/12 424/605 |

OTHER PUBLICATIONS

PCT Notification of Transmittal, the International Search Report and the Written Opinion issued in connection with PCT/US18/54515, filed Oct. 5, 2017, which was dated Dec. 21, 2018 (11 pages).

* cited by examiner

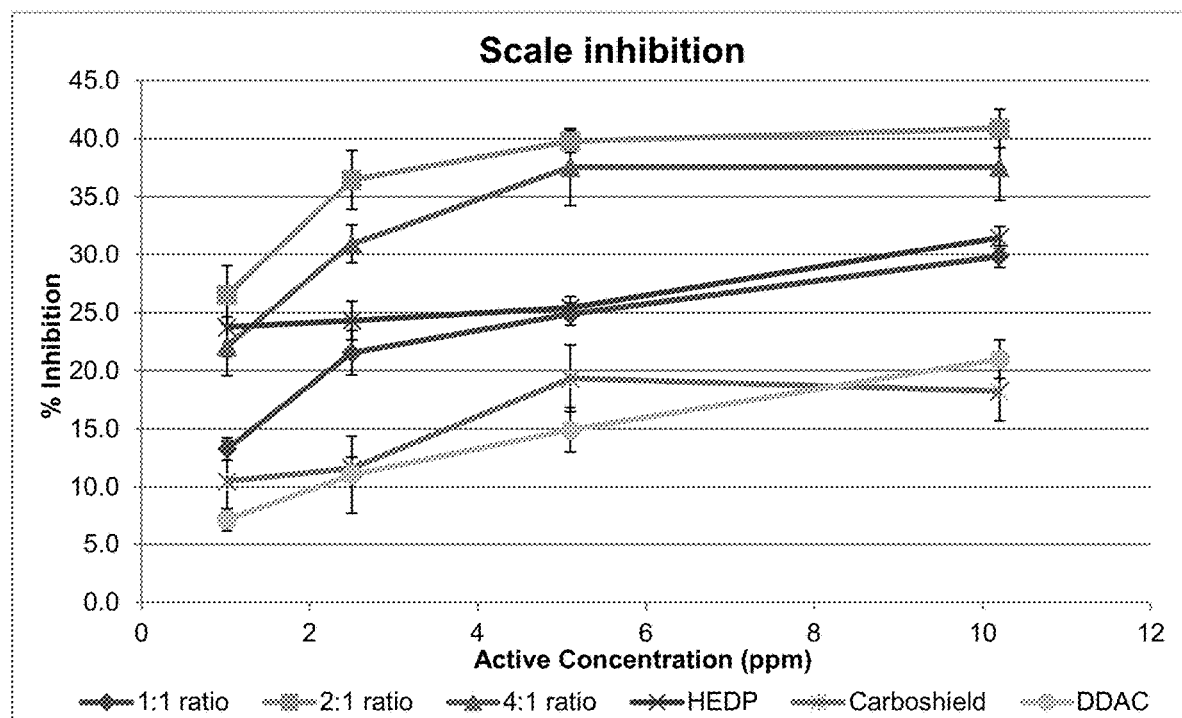

QUATERNARY AMMONIUM ETIDRONATES

CROSS-REFERENCE TO RELATED APPLICATIONS

The present application is based upon and claims priority to U.S. Provisional Application Ser. No. 62/568,595, filed on Oct. 5, 2017, which is incorporated herein by reference.

FIELD OF INVENTION

The disclosure relates to quaternary ammonium etidronates (QAE), the method of preparing quaternary ammonium etidronates and methods of using the same.

BACKGROUND OF THE INVENTION

Quaternary ammonium chlorides have been used in a variety of different products including surfactants, antimicrobial compositions, antiseptic compositions, water treatment compositions, and other biocidal compositions. However, quaternary ammonium chlorides, while effective antimicrobial agents, have a drawback in that the dissociation of the chloride ions in solution results in the corrosion of metal surfaces.

To address this corrosion problem with quaternary ammonium chlorides, other quaternary ammonium compounds have been developed. One class of quaternary ammonium compounds is quaternary ammonium carbonates/bicarbonates. Unlike traditional quaternary ammonium chlorides, quaternary ammonium carbonates/bicarbonates provide solutions which exhibit excellent corrosion inhibitory properties on a wide variety of metal substrates. However, quaternary ammonium carbonates/bicarbonates suffer from one drawback also, whereby in hard water, the carbonate/bicarbonate salts tend to form scale, due to the presence of calcium in the water.

There is a need in the art to have a quaternary ammonium compound which will provide both low corrosion and low scale in systems which contain metal surfaces. The present disclosure provides an answer to that need of identifying a quaternary ammonium compound with anti-corrosive properties, biocidal activity and low scaling properties.

It has now been surprisingly found that quaternary ammonium etidronates or derivatives thereof may be used in lieu for quaternary ammonium chlorides and quaternary ammonium carbonate/bicarbonate, by eliminating the presence of chloride ions and carbonates/bicarbonate ions, which currently result in the issue of scaling in hard water and metal corrosion.

SUMMARY OF THE INVENTION

The present invention, in one embodiment, describes quaternary ammonium etidronate compounds (QAE) having a quaternary ammonium cation, and an etidronate anion. Variable ratios of each reactant, as further described, can be reacted together, resulting in the formation of different quaternary ammonium etidronates. Furthermore, the method of preparation and use of QAE compounds is also described.

In accordance with the present invention, describes the quaternary ammonium etidronate compounds, having the Formula I, having of a quaternary ammonium cation and an etidronate anion as shown below:

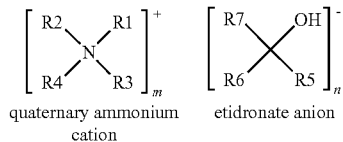

quaternary ammonium cation    etidronate anion

[I]

wherein the quaternary ammonium cation having the Formula I, R1 or R2, is a H or a substituted or unsubstituted straight chain or branched $C_1$-$C_8$ alkyl, aryl, alkylaryl/arylalkyl, cycloalkyl, (aromatic or non-aromatic) heterocyclyl, or alkoxy; a or b is any integer of 1 or greater;

R3 or R4 is a substituted or unsubstituted straight chain or branched $C_6$-$C_{30}$ alkyl, aryl, alkylaryl/arylalkyl, cycloalkyl, (aromatic or non-aromatic) heterocyclyl, alkenyl, phenyl, alkyl-substituted phenyl, benzyl, naphthylmethyl, or ethylbenzyl group;

wherein two or more of R1, R2, R3 or R4 may together with a nitrogen atom form a substituted or unsubstituted heterocyclic ring; and wherein the total number of carbon atoms in the groups R1, R2, R3 or R4 must be at least 12;

wherein the etidronate anion, having the Formula I, is an etidronic acid or salt thereof wherein R5 and R6 is $PO_3^{2-}$ or $PO_3X_y$; wherein each X is a H, M, H$^-$, HM, M$^-$ or M$^+$; wherein y is 0-2; and M is lithium, sodium, potassium or any combinations thereof; and wherein R7 group is a H or a substituted or unsubstituted straight chain or branched $C_1$-$C_8$ alkyl; and wherein m is 1-4 and n is 1.

In another embodiment, R1, R2, R3 or R4 when substituted comprises substituent groups selected from one or more of a F, Br, Cl, OR', NR'R'', $CF_3$, CN, $NO_2$, C2R', SR', N3, C(=O)NR'R'', NR'C(O)R'', O(CR'R'')rC(=O)R', O(CR'R'')rNR'C(O)R', (CR'R'')rNR''$SO_2$R', OC(O)NR'R'', NR'C(O)OR'', $SO_2$R', $SO_2$NR'R'', NR'$SO_2$R''; or combinations thereof; wherein R' and R'' are individually hydrogen, $C_1$-$C_8$ alkyl, cycloalkyl, heterocyclyl, aryl, or arylalkyl, and r is an integer from 1 to 6, or R' and R'' together form a cyclic functionality.

In one embodiment, R1 and R2 are each a $CH_3$.

In one embodiment, R3 and R4 are each a substituted or unsubstituted straight chain or branched $C_6$-$C_{30}$ alkyl, aryl, alkylaryl/arylalkyl, cycloalkyl, (aromatic or non-aromatic) heterocyclyl, alkenyl, phenyl, alkyl-substituted phenyl, benzyl, naphthylmethyl, or ethylbenzyl group.

In one embodiment, quaternary ammonium cation, comprises a $C_8$-$C_{30}$ dialkyldimethyl ammonium, $C_8$-$C_{30}$ dialkylmethylpoly(oxyethyl) ammonium, $C_8$-$C_{30}$ alkylbenzyldimethyl ammonium, $C_8$-$C_{30}$ alkyltrimethylammonium, $C_8$-$C_{30}$ dialkyldihydroxyethyl ammonium, $C_8$-$C_{30}$ dialkylmethylhydroxyethyl ammonium, or $C_8$-$C_{30}$ alkylmethyldihydroxyethyl ammonium.

Another aspect provides, a method of preparing such compounds is described, by reacting a quaternary ammonium cation with an etidronate anion, to form the quaternary ammonium etidronate compound as shown in Schematic A; wherein the quaternary ammonium compound reactant or etidronate anion is present at variable ratios; and wherein Y is an anion.

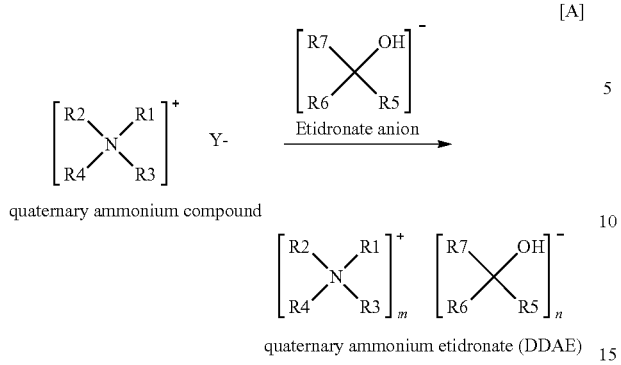

Schematics for the reaction of a quaternary ammonium compound and etidronate anion to form DDAE.

In one embodiment, the weight ratio of the quaternary ammonium cation to the etidronate anion is from about 1:1 to about 4:1.

In one particular embodiment, the etidronate anion comprises an ion of 1-hydroxyethane 1,1-diphosphonic acid (HEDP or etidronic acid), sodium etidronate, disodium etidronate (1-Hydroxyethanediphosphonic acid, sodium salt), dilithium etidronate, dipotassium etidronate, trisodium etidronate, tetrasodium etidronate, tetrapotassium etidronate or combinations thereof.

In further embodiments, the reaction, according to the method described, takes places in the presence of optional additives comprising antifoaming agents, base, aqueous solvent or combinations thereof.

In yet another embodiment, the application for such compounds is described for use in various compositions such as water treatment, personal care, cosmetics, wood treatment, paint, coatings, agrochemicals, antimicrobial, disinfectant, hygiene compositions, biocidal compositions or combinations thereof.

In one aspect of the present invention, an effective amount of one or more quaternary ammonium etidronate is added, wherein the compound is contacted for an amount of time sufficient to kill microbes present in the water, and wherein the water is a swimming pool, pond, lake, stream or canal.

Another aspect of the present invention describes a water treatment composition comprising an effective amount of one or more of a quaternary ammonium etidronate compound or derivative thereof, and a water treating biocidal agent.

In a further aspect, the invention provides a water treatment composition comprising (a) an effective amount of one or more of a quaternary ammonium etidronate compound or derivative thereof, according to the present invention, (b) a water treating biocidal agent, (c) a hydrogen peroxide source and (d) water.

In one embodiment, the water treating biocidal agent comprises a halogen releasing agent; a peroxy compound; a hydrogen peroxide source; an isothiazolone, derivatives or a mixture of isothiazolones; an amine, or combinations thereof.

In a particular embodiment, the halogen releasing agent comprises a chlorinated isocyanuric acids or salts thereof, halogenated hydantoins, hypochlorous acid, hypochlorite salts, chlorine gas, chlorine dioxide, hypobromite salts, hypobromous acid or a mixture thereof.

In one embodiment, a water treatment, cosmetic, hygiene, personal care, paint, coating, wood treatment, agrochemical, antimicrobial, biocidal or disinfectant composition comprising an effective amount of one or more quaternary ammonium etidronate compounds, useful as a disinfectant, decontaminant, microbial agent, sanitizer or cleaning agent.

In one aspect, the invention provides quaternary ammonium etidronate compounds, having high anti-corrosive properties, biocidal properties and low scaling properties.

These and other aspects will become apparent when reading the detailed description of the invention.

BRIEF DESCRIPTION OF THE DRAWING

FIG. 1 shows the scale inhibition (%) of the samples at different concentrations.

DETAILED DESCRIPTION

The present invention encompasses quaternary ammonium salts of etidronic acid or salts thereof and a method for the preparation of such quaternary etidronate compounds. One unique aspect of the present invention is that the inventive compound does not contain corrosive and scaling counter ions of quaternary ammonium chloride and carbonates/bicarbonates, when used on metal surfaces. The elimination of these by-product formations advantageously provides a greater degree of anti-corrosive and low scaling properties.

Furthermore, another embodiment provides the use of such compounds in combination with a hydrogen peroxide source and/or other acids for water treatment applications such as cooling towers and recirculating water systems. This embodiment provides a method of disinfecting a surface of microorganisms by contacting the surface with the disinfecting composition for an amount of time effective to kill a majority of the microbes located on the surface, is further described.

In accordance with the present invention, the quaternary ammonium etidronate compounds, having the Formula I, having of a quaternary ammonium cation and an etidronate anion is shown below:

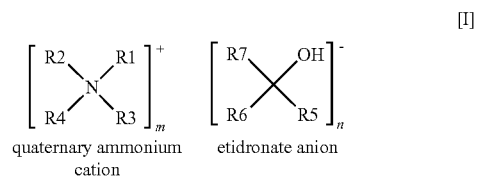

wherein the quaternary ammonium cation having the Formula I, R1 or R2, is a H or a substituted or unsubstituted straight chain or branched $C_1$-$C_8$ alkyl, aryl, alkylaryl/arylalkyl, cycloalkyl, (aromatic or non-aromatic) heterocyclyl, or alkoxy; a or b is any integer of 1 or greater;

R3 or R4 is a substituted or unsubstituted straight chain or branched $C_6$-$C_{30}$ alkyl, aryl, alkylaryl/arylalkyl, cycloalkyl, (aromatic or non-aromatic) heterocyclyl, alkenyl, phenyl, alkyl-substituted phenyl, benzyl, naphthylmethyl, or ethylbenzyl group;

wherein two or more of R1, R2, R3 or R4 may together with a nitrogen atom form a substituted or unsubstituted heterocyclic ring; and wherein the total number of carbon atoms in the groups R1, R2, R3 or R4 must be at least 12;

wherein the etidronate anion, having the Formula I, is an etidronic acid or salt thereof wherein R5 and R6 is $PO_3^{2-}$ or PO₃X_y; wherein each X is a H, M, H⁻, HM, M⁻ or M⁺; wherein y is 0-2; and M is lithium, sodium, potassium or any combinations thereof; and wherein R7 group is a H or a substituted or unsubstituted straight chain or branched $C_1$-$C_8$ alkyl; and wherein m is 1-4 and n is 1.

Alternately, the quaternary ammonium cation having the groups R1, R2, R3 and R4, may each independently be a substituted or unsubstituted straight chain or branched alkyl, aryl, alkylaryl, arylalkyl, cycloalkyl, (aromatic or non-aromatic) heterocyclyl or alkenyl group. In a one aspect of the present invention, at least one of the groups R1 and R2 contains 1-8 carbon atom and R3 and R4 each independently contain from $C_6$-$C_{30}$ carbon atoms.

For example, there are at least 1 and up to 8 carbon atoms for R1 and R2, generally 1 to 6 carbon atoms, typically 1 to 4 carbon atoms; and R3 and R4 each independently contain from $C_6$-$C_{30}$, generally $C_5$-$C_{22}$.

In the present invention, one embodiment of the quaternary ammonium cation having the Formula I, where R1 and R2 are each independently a $C_1$-$C_6$ substituted or unsubstituted alkyl. In another embodiment, R1 and R2 may be the same $C_1$-$C_6$ alkyl group. Desirably, each of R1 and R2 group is $CH_3$.

The quaternary ammonium cation, shown in Formula I, includes, but is not limited to, one in which R3 and R4 is a substituted or unsubstituted and/or straight chain or branched $C_5$-$C_{30}$ alkyl, aryl, alkylaryl, arylalkyl, cycloalkyl, (aromatic or non-aromatic) heterocyclyl, alkenyl, phenyl, alkyl-substituted phenyl, benzyl, naphthylmethyl, or ethylbenzyl group. Such as a $C_5$-$C_{30}$ dialkyldimethyl ammonium, $C_5$-$C_{30}$ dialkylmethylpoly(oxyethyl) ammonium, $C_5$-$C_{30}$ alkylbenzyldimethyl ammonium, $C_5$-$C_{30}$ alkyltrimethylammonium, $C_5$-$C_{30}$ dialkyldihydroxyethyl ammonium, $C_5$-$C_{30}$ dialkylmethylhydroxyethyl ammonium, $C_5$-$C_{30}$ alkylmethyldihydroxyethyl ammonium or combinations thereof, and the like.

Suitable examples of quaternary ammonium cations include, but not limited to, [2-[2-(4-diisobutylphenoxy)ethoxy] ethyl] dimethylbenzyl ammonium, N,N-didecyldimethyl ammonium, N,N-dioctyldimethyl ammonium, N,N-octyldecyldimethyl ammonium, octadecyldimethylbenzyl ammonium, N,N-decylisononyldimethyl ammonium, hexadecyltrimethyl ammonium, N,N-didecyl-N-methyl-poly(oxyethyl) ammonium, alkyldimethylbenzyl ammonium, didecylmethylhydroxyethyl ammonium or combinations thereof, and the like.

Desirably, the quaternary ammonium cation comprises N,N-dialkyldimethylammonium cation.

As further described, the present invention describes a quaternary ammonium cation, shown in Formula I, whereby the quaternary ammonium compound is generated from a quaternary ammonium compound, having a Y⁻ anion, wherein the anion source includes, but not limited to, a quaternary ammonium carbonates, bicarboantes, halides, phosphates, sulfates, bisulfates, acetates, nitrates, hydroxides, salicylates, bentonites, molybdates, formates, borates, sulfonates, phosphites, hypophosphite, or combinations thereof, and the like.

Suitably, the quaternary ammonium etidronate compounds are generated from quaternary ammonium carbonates, as shown in Schematic A and B.

Typically, the quaternary ammonium cation having groups R1, R2, R3, or R4 may have suitable substituents groups attached to the selected groups on the R1, R2, R3 and R4 groups. For example, any one of R1, R2, R3, or R4 when substituted comprises substituent groups selected from one or more of a F, Br, Cl, I, —OR', —NR'R", —CF₃, —CN, —NO₂, —C₂R', —SR', —N₃, —C(=O)NR'R", —NR'C(O)R", —O(CR'R")rC(=O)R', O(CR'R")rNR'C(O)R', —(CR'R")rNR"SO₂R', —OC(O)NR'R", —NR'C(O)OR", —SO₂R', —SO₂NR'R", and —NR'SO₂R", wherein R' and R" are each individually hydrogen, $C_1$-$C_8$ alkyl, cycloalkyl, heterocyclyl, aryl, or arylalkyl, and r is an integer from 1 to 6, or R' and R" together form a cyclic functionality.

The etidronate anion, shown in Formula I, is typically derived from etidronic acid or an etidronate salt, to prepare the quaternary ammonium etidronate (QAE). The groups R5 and R6 are each independently $PO_3^{2-}$ or $PO_3X_y$; where y is between 0-2, and where each X is independently a H, M, H⁻, M⁻, HM, or M⁺; as described above; and R7 group is independently a H or a substituted or unsubstituted straight chain or branched $C_1$-$C_8$ alkyl. Suitably, M is lithium, sodium, potassium or any combinations thereof.

Desirably, the etidronate anion shown in Formula I, is one in which the group R5 is $PO_3^{2-}$, $PO_3H_2$, $PO_3M_2$, $PO_3HM$, $PO_3H^-$, or $PO_3M$; the group R6 is $PO_3^{2-}$, $PO_3H_2$, $PO_3M_2$, $PO_3HM$, $PO_3H^-$, or $PO_3M^-$, and R7 is $CH_3$.

Examples of etidronate anion include, but are not limited to, 1-hydroxyethane 1,1-diphosphonic acid (HEDP or etidronic acid), sodium etidronate, disodium etidronate (1-Hydroxyethanediphosphonic acid, sodium salt), dilithium etidronate, dipotassium etidronate, trisodium etidronate, tetrasodium etidronate, tetrapotassium etidronate or combinations thereof, and the like. Desirably, the etidronate anion is etidronic acid (1-hydroxyethane 1,1-diphosphonic acid, HEDP).

In schematic A below, an indirect synthesis method may be used to prepare the quaternary ammonium etidronates compounds of the present invention. The starting components used to prepare quaternary etidronate compounds may be prepared by conventional means known to those of ordinary skill in the art, such as those shown in U.S. Pat. No. 6,080,789A, 5,438,034A, 5,399,762A, 6,399,827B1, PCT publication WO2009/038919A1, and Japanese patent JP09077610, each is hereby incorporated by reference it its entirety. The product yield can be further improved by adjusting the amount of reactants used, as variable ratios of each reactant to form QAE are further described.

As previously mentioned, the quaternary etidronate compounds may be prepared by a variety of methods. The present invention also provides a method of reacting the quaternary ammonium etidronate compound (QAE) with an etidronate anion, as shown in Schematic A below. Suitably, the ratio of quaternary ammonium compound and etidronate anion may vary in an amount at variable ratios from about 1:1 to about 4:1 of quaternary ammonium compound and etidronate anion; where m is 1-4 and n is 1; and wherein Y⁻ is an anion.

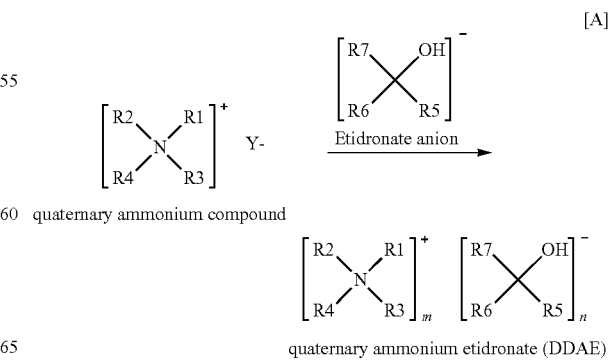

[A]

quaternary ammonium compound quaternary ammonium etidronate (DDAE)

Schematics for the reaction of a quaternary ammonium compound and etidronate anion to form DDAE.

Typically, the Y⁻ anion, includes, but is not limited to, carbonates, bicarboantes, halides, phosphate, sulfates, bisulfate, acetate, nitrates, hydroxides, salicylates, bentonites, molybdates, formate, borates, sulfonates, phosphites, hypophosphite, or combinations thereof. Suitably, the quaternary ammonium compound being a quaternary ammonium carbonate.

Alternately, the quaternary ammonium compound is a quaternary ammonium hydroxide formed by initially reacting a metal hydroxide such as NaOH with a quaternary ammonium carbonate, bicarbonate, sulfate or nitrate and the like.

Suitably, the etidronate anion includes, but is not limited, to 1-hydroxyethane 1,1-diphosphonic acid (HEDP or etidronic acid), sodium etidronate, disodium etidronate (1-Hydroxyethanediphosphonic acid, sodium salt), dilithium etidronate, dipotassium etidronate, trisodium etidronate, tetrasodium etidronate, tetrapotassium etidronate or combinations thereof, and the like. Desirably, the etidronate anion comprises etidronic acid (1-hydroxyethane 1,1-diphosphonic acid, HEDP).

For example, one particular method of preparing the quaternary ammonium compounds (QAE), having the Formula I, as shown in the reaction Scheme B includes reacting a quaternary ammonium carbonate and/or bicarbonate (such as didecyldimethylammonium carbonate, DDAC) with etidronic acid in an aqueous solvent, resulting in the production of various molar ratios of DDAE (Formula A, B, C or D) of about 1:1 to about 4:1; as described in Scheme B. The reaction products with Formula A, B, C or D can be further converted into its alkali metal forms of Formula I-V respectively, using alkali metal hydroxide, wherein M is lithium, potassium or sodium, as further described.

The reaction, as shown in Schematic B above, is stirred in the presence of an aqueous solvent, and from about 20° C., to an elevated temperature up to about 90° C., and held at that temperature for a period of about 1 hour to about 5 hours, after which, the reaction mixture is then cooled to room temperature. The order of addition of reactants or solvent in any individual step does not affect the process. Reactants or solvent can be added sequentially or simultaneously in any suitable reaction vessel. Importantly, the method of the present invention is suitable for commercial scale production techniques and equipment, yet convenient for small scale work.

For example, in the process of reacting a quaternary ammonium compound such as didecyldimethyl ammonium carbonate with HEDP; there is an exchange of carbonate and/or bicarbonate anions of quaternary ammonium carbonate with HEDP. The reaction involves complete neutralization of carbonate or bicarbonate of the quaternary ammonium carbonate with HEDP to produce quaternary ammonium etidronate by releasing carbon dioxide gas (product generated through the reaction process). The structure identity of the quaternary ammonium etidronates is determined by the molar ratio of quaternary ammonium carbonate to HEDP and HEDP/base or pH.

QAE may also be produced through other known methods as shown by WO 2009/038919A1, U.S. Pat. No. 6,399,827B1, JP 09077610 and others. Through this process, equivalent amounts of an alkali metal hydroxide and a quaternary ammonium halide, sulfate or nitrate is reacted to generate the quaternary ammonium hydroxide. The quaternary hydroxide is filtered, removing alkali metal halides, sulfates or nitrates, after which the filtrate is reacted with etidronic acid to produce the quaternary ammonium etidronate.

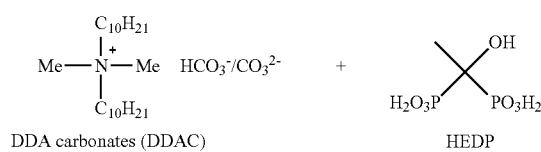
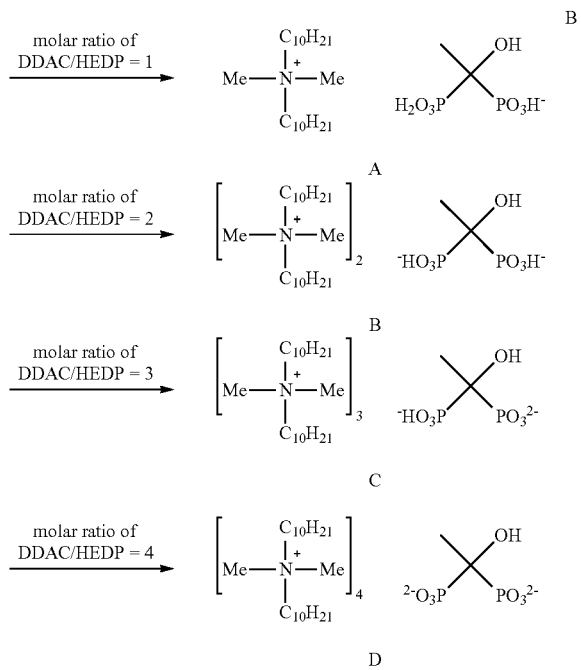

lp;.5p

Schematics for the reaction of a quaternary ammonium compound and etidronate anion to form various molar ratio of DDAE.

In another embodiment, for example, QAE may also be formed through a two-step reaction process; whereby the first step involves the reaction of decyldimethylamine with decyl chloride in an alcohol such as methanol or ethanol, at an elevated temperature, after which a base such as sodium hydroxide is added to the solvent to neutralize acidic solution. The second step involves the removal of the resulting sodium chloride via filtration, followed by the addition of etidronic acid to the filtrate containing didecyldimethylammonium hydroxide forming one or more of a QAE compound, having the Formula I.

The method of forming QAE further comprises the reaction taking place in the presence of one or more of an aqueous solvent, optional anti-foaming agent, optional base or combinations thereof, and the like. The addition of one or more of the following are each dependent on the ratio of quaternary ammonium reactant and etidronate reactant used.

Examples of aqueous solvent include, but is not limited to, water, aqueous alcohols, ammonia water, acid solutions, salt solutions, water-miscible organic solvents, glycols (i.e. ethylene glycol, propylene glycol), combinations thereof, and the like. Suitably, the solvent used is water or an aqueous alcohol.

Examples of aqueous alcohols include, but are not limited to, methanol, ethanol, propanol, benzyl alcohol, phenoxyethanol, isopropanol, ethylene glycol, propylene glycol or combinations thereof, and the like.

Examples of water-miscible organic solvents include, but not limited to, alkyl and dialkly glycol ethers of ethylene glycol or propylene glycol, such as diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, tripropylene glycol methyl ether, dipropylene glycol methyl ether, dipropylene glycol butyl ether, or combinations thereof, and the like.

The addition of a base (strong or weak) is needed to neutralize the presence of excess acid group of etidronates in the reaction vessel. Examples of a strong or weak base includes, but is not limited to, NaOH, KOH, LiOH, NH$_4$OH, ammonia or combinations thereof, and the like. Suitably, the base comprises 50% NaOH.

The addition of an anti-foaming agent is optional; examples of anti-foaming agents include, but are not limited to, silicon based (polydimethylsiloxane, Orco Antifoam AFB™, Andifoam-DF series; Foam Blast or Masil series by Emerald Performance materials; SAF series by Silchem Inc.; Silfar series by Wacker Chemical Corp.; or etc.), alkyl poly acrylates, castor oil, fatty acids, fatty acids esters (saturated or unsaturated $C_4$-$C_{22}$ atoms; polymerized $C_4$-$C_{22}$ fatty acid esters), mineral oils, fatty acids sulfate, fatty alcohols ($C_{12}$-$C_{30}$ monohydric to trihydric alcohols $C_4$-$C_{22}$ monohydric to trihydric alcohols), fatty alcohol esters (dihydric or trihydric alcohols of $C_{12}$ to $C_{22}$ atoms; polyoxypropylated or ethoxylated glycerol; saturated or unsaturated $C_4$-$C_{22}$ atoms), fatty alcohol sulfate, foot olive oil, mono & diglyceride, paraffin oil, paraffin wax, polypropylene glycol, vegetable oil (cottonseed oil or etc.), polyols, polyglycerol fatty acid esters of $C_4$-$C_{22}$ atoms, and the like. In one embodiment of this present invention, the antifoaming agent is polydimethylsiloxane, (Trade name SAG 710 antifoam). As previously mentioned above, the addition of the anti-foaming agent will be dependent on the ratio of quaternary ammonium cation salt and etidronate anion as shown in the examples to follow.

Furthermore, the percent yield of quaternary ammonium cation formed is dependent on the quaternary ammonium compound and etidronate used; generally the conversion is quantitative, as shown in Schematic B.

For example, the percent yield of quaternary ammonium cation formed from the reaction process ranging from about 31% to about 45%, is dependent on the molar ratio of quaternary ammonium reactant and etidronic acid used to form the quaternary etidronate compound. In addition, the present invention describes the need to adjust the pH of the solution, which will also vary depending on the ratio of quaternary ammonium cation to etidronate anion and the addition of NaOH to neutralize the OH$^-$ anions at R5 and R6 group, as shown in Formula I.

For example, didecyldimethylammonium etidronates having Formula II, III, IV, or V, are generated from the reaction using various ratios of quaternary ammonium compound such as didecyldimethyl ammonium carbonate and etidronic acid in the presence of water and an optional antifoaming agent (for example a polydimethylsiloxane, Trade name SAG 710 antifoam) using about 1 to about 4 molar ratios of didecyldimethyl ammonium carbonate to etidronic acid, respectively. Consequently, an alkali metal hydroxide is added to afford the corresponding M salts of Formula II, III, IV or V; whereby M is lithium, sodium or potassium salt.

Suitably, the ratio of quaternary ammonium cation and etidronate anion can be present at variable ratios from about 1:1 to about 4:1. For example, typically the ratio from about 1 to about 1 of quaternary ammonium carbonate cation and etidronic acid may be used to form the quaternary etidronate compounds, having the Formula I. In this example the group R5 may be any one of PO$_3^{2-}$, PO$_3$M$_2$, or PO$_3$HM, the group R6 may be any one of PO$_3$H$^-$ or PO$_3$M$^-$ and R7 is CH$_3$.

In one particular embodiment, for example, the QAE compound formed from the 1:1 ratio of quaternary ammonium carbonate cation to etidronate anion, is one having the Formula II, wherein the group R5 is PO$_3$M$_2$, the group R6 is PO$_3$M$^-$ and the group R7 is CH$_3$, as shown below, where m and n are independently 1.

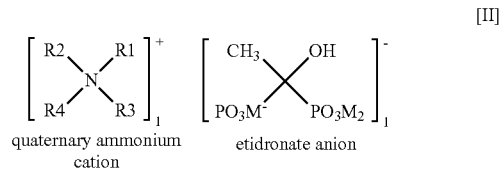

For example, the preparation of QAE using such a ratio includes the mixture of about 1 molar ratio of quaternary ammonium carbonate cation salt, about 1 molar ratio etidronate anion, water, and polydimethylsiloxane antifoam at about 20° C. to about 90° C., for about 1 to about 5 hr., to form a quaternary etidronate compound, having the Formula I, wherein R5 is PO$_3^{2-}$, PO$_3$M$_2$, or PO$_3$HM, R6 is PO$_3$H$^-$ or PO$_3$M$^-$ and R7 is CH$_3$.

Typically the ratio of about 2 to about 1 ratio of reacting quaternary ammonium carbonate cation with etidronate anion may be used to form the quaternary etidronate compound, having the Formula I. For example, the preparation of QAE involves mixing about 2 molar ratio of quaternary ammonium carbonate cation salt, about 1 molar ratio etidronate acid, water, and polydimethylsiloxane antifoam at about 20° C. to about 90° C. for about 1 to about 5 hr., to form a quaternary etidronate compound, having the Formula II, wherein the group R5 is $PO_3H^-$, or $PO_3M^-$, the group R6 is $PO_3H^-$ or $PO_3M-$ and the group R7 is $CH_3$.

Additionally, the QAE formed from the 2:1 ratio of quaternary ammonium carbonate to etidronate anion, is one having the Formula III, wherein the group R5 and R6 are each $PO_3M^-$, R7 is $CH_3$, m is 2 and n is 1.

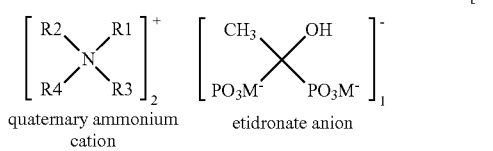

quaternary ammonium cation    etidronate anion    [III]

Typically the ratio of about 3 to about 1 ratio of reacting quaternary ammonium carbonate cation with etidronate anion may be used to form the quaternary etidronate compound, having the Formula I. For example, the preparation of QAE involves mixing about 3 molar ratio of quaternary ammonium carbonate cation salt, about 1 molar ratio etidronate acid, water, and polydimethylsiloxane antifoam at about 20° C. to about 90° C., for about 1 to about 5 hr., to form a quaternary etidronate compound, having the Formula I, wherein R5 is $PO_3^{2-}$ and R6 is $PO_3H^-$ or $PO_3M^-$.

For example, the QAE formed from the 3:1 ratio of quaternary ammonium carbonate cation to etidronate anion, is one having the Formula IV, wherein the group R5 is $PO_3M^-$, R6 is $PO_3^{2-}$, R7 is $CH_3$, m is 3 and n is 1.

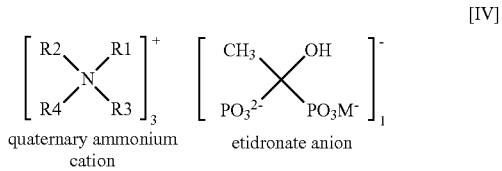

quaternary ammonium cation    etidronate anion    [IV]

Typically, the ratio of about 4 to about 1 ratio of reacting quaternary ammonium carbonate cation with etidronate acid may be used to form the quaternary etidronate compound, having the Formula I. For example, the preparation of QAE involves mixing about 4 molar ratio of quaternary ammonium carbonate cation salt, about 1 molar ratio etidronate anion, water, and polydimethylsiloxane antifoam at about 20° C. to about 90° C., for about 1 to about 5 hr., to form a quaternary etidronate compound, having the Formula I, wherein the group R5 is $PO_3^2$ and the group R6 is $PO_3^{2-}$.

For example, the QAE formed from the 4:1 ratio of quaternary ammonium carbonate cation to etidronate anion, is one having the Formula V, wherein the group R5 and R6 group are each $PO_3^{2-}$, R7 is $CH_3$, m is 4 and n is 1.

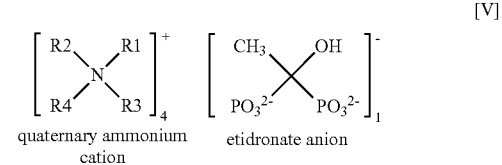

quaternary ammonium cation    etidronate anion    [V]

In another aspect of the present invention, the QAE compound provides high anti-corrosive properties, biocidal properties, and low scaling properties in comparison to quaternary ammonium carbonates; as shown in FIG. 1. Furthermore, the QAE compound in the present invention may be used in various applications, in lieu of carbonate quaternary ammonium compounds.

In one aspect, the present invention may be used in various application areas including, but not limited to, water treatment systems, cosmetic, hygiene, personal care, paint, coating, wood treatment, agrochemical, antimicrobial, biocidal or disinfectant composition, and the like. Such application having an effective amount of one or more QAE compounds are useful as a disinfectant, decontaminant, microbial agent, sanitizer, cleaning agent, and the like. Additionally such compositions are contacted for an amount of time, effective to kill a majority of the microbes located on the surface or in the formulations.

For example, the QAE compound formed from the methods described above may be applied, to formulations/compositions where quaternary ammonium carbonate is currently being used, such as, water treatment systems, personal care, cosmetics, wood treatment, and hygiene compositions, biocidal compositions, other water treatment compositions, and the like. The compositions, as described in this present invention, may be used in concentrated or diluted forms depending upon the application.

Additionally, the low scaling properties of the QAE compounds are demonstrated. As shown in FIG. 1 the scale inhibition test demonstrates that all DDA etidronates (1:1, 2:1, and 4:1 ratios) showed 20-25% more scale inhibition in comparison with Carboshield 1000 and DDAC within the tested ranges of concentrations; which both exhibited little to no scale inhibition. In comparison with HEDP, the 1:1 ratio appeared to show a similar % inhibition as HEDP, and the 2:1 ratio and the 4:1 ratio DDA etidronate appeared to show better inhibition performance than HEDP. The 2:1 ratio seemed to perform the best for scale inhibition based on total active concentrations. These results indicate the synergistic effect with the DDAE samples, in particular with the 2:1 and 4:1 ratio; while Carboshield and DDAC showed the lowest performance for scale inhibition.

In one embodiment, a water treatment composition is described using a QAE or derivative thereof, and a water treating biocidal agent. The water treatment composition is formed containing an effective amount of a QAE compound or derivative thereof, and a water treating biocidal agent.

Desirably, a method of treating as cooling towers and recirculating water systems comprising an effective amount of one or more QAE compounds; wherein the compound(s) is contacted for an amount of time sufficient to kill microbes present in the water The water treating biocidal agent includes, but is not limited to, halogen releasing agent; an amine (such as Bis (3-aminopropyl) dodecylamine); a peroxy acids or salts thereof (such as persulfates, persalts and halide salts); hydrogen peroxide source, an isothiazolinone or a mixture of isothiazolinones; or combinations thereof and the like, or compatible combinations thereof.

Examples of exemplary halogen releasing agents include, but are not limited to, chlorinated isocyanuric acids or salts thereof, halogenated hydantoins, hypochlorous acids or salts thereof, chlorine gas, chlorine dioxide, hypobromite salts, hypobromous acid; and compatible combinations thereof.

Examples of isocyanuric acids or salts thereof, include but are not limited to, such as trichloroisocyanuric acid (TCCA), dichloroisocyanuric acid (DCCA), dichloroisocyanurate salts (e.g. sodium dichloroisocyanurate, potassium dichloroisocyanurate), trichloroisocyanurateand (e.g. sodium or potassium trichloroisocyanurate), or combinations thereof, and the like.

Examples of halogen-containing hydantoins include, but are not limited to, both chlorine-containing hydantoins and bromine-containing hydantoins such as bromochlorodimethylhydantoin (BCDMH), dibromodimethylhydantoin (DBDMH), dichlorodimethylhydantoin (DCDMH), dichloromethylethylhydantoin (DCMEH), or combinations thereof, and the like.

Examples of hypochlorous acids or salts thereof include, but are not limited to, lithium hypochlorite, sodium hypochlorite, potassium hypochlorite, magnesium hypochlorite, calcium hypochlorite, or combinations thereof, and the like.

Examples of hydrogen peroxide sources include, but are not limited to, aqueous hydrogen peroxide solution, sodium percarbonate, potassium percarbonate, sodium and potassium perborate, hydrogen peroxide urea, as well as their hydrated forms, or combinations thereof and the like. For example, one hydrogen peroxide source comprises a concentrated solution containing about 20% to about 50 w/w % of a hydrogen peroxide source dissolved in water. For example, another composition the hydrogen peroxide source comprises a solid formulation of sodium percarbonate.

For example, a method of treating water systems comprising the quaternary ammonium etidronate compound or derivative thereof present from about 5 w/w % to about 35 w/w % of the total composition; and the water treating biocidal agent is present from about 0.1 w/w % to 25 w/w % of the total composition.

Specifically, a biocidal or water treatment composition comprising 5 w/w % to about 35 w/w % of a quaternary ammonium etidronate compound and a hydrogen peroxide present in an amount from 0.1 w/w % to about 25 w/w % of a concentrated hydrogen peroxide source ranging from 20 w/w % to 50 w/w %.

Suitably, a biocidal composition is provided comprising 25% of about a 2 to about a 1 ratio of QAE composition and about 16% of a 50% concentrated hydrogen peroxide source dissolved in water.

Furthermore, such water treating systems may further comprise an optional acid, a carboxylic acid or mineral acid; optional stabilizer; second biocidal agent or combinations thereof and the like.

The total concentration of the acid is present from about 0.1 w/w % to 10 w/w % of the total composition. Examples of carboxylic acids include but not limited to, a $C_1$ to $C_8$ mono, di- or tricarboxylic acid, a $C_1$ to $C_8$ hydroxyl carboxylic acid, a substituted or unsubstituted aromatic carboxylic acid such as acetic acid, propionic acid, butyric acid, pentanoic acid, hexanoic acid, octanoic acid, succinic acid, citric acid, oxalic acid, tartaric acid, glutaric acid, adipic acid, benzoic acid, phthalic acid, or combinations thereof, and the like.

Examples of mineral acids include, but not limited to, phosphoric acid, sulfuric acid, hydrochloric acid or combinations thereof, and the like. The total concentration of the acid is present from about 0.1 w/w % to 10 w/w % of the total composition.

Examples of the second biocidal agent include, but are not limited to, isothiazolones or combinations thereof; pyrithiones, halogenated hydantoins, isocyanuric acids or salts thereof; hypochlorous or hypobromous acid and salts thereof; glutaraldehyde, Iodopropynyl butylcarbamate (IPBC), polyhexamethylene biguanide (PHMB), 2-Bromo-2-nitro-1,3-propanediol (bronopol), 2,2-dibromo-3-nitrilopropionamide (DBNPA), or combinations thereof, and the like. The second biocide may be present from about 0.1 w/w % to about 25 w/w % of the total composition.

Examples of optional stabilizer include, but are not limited to, organic and inorganic sequestering agent such as stannates and phosphates, and/or combinations of organic compounds, organometallic salts and metal chelators with or without stannates or phosphates; combinations thereof, and the like. The addition of a stabilizer(s) serves to prevent the components, in the biocidal composition, from decomposing on the shelf prematurely during storage of the formulations.

For example, the addition of a stabilizer is used to deactivate impurities that may cause decomposition of hydrogen peroxide source. The amount of the stabilizer in the concentrate may be from about 0.01 w/w % to about 5 w/w %.

Suitably, the concentration of stabilizer used may be from about 0.05 w/w % to about 2 w/w %; or desirably from about 0.1 w/w % to about 1.0 w/w %.

Other additives may be also added to the biocidal composition of the present disclosure, to provide the composition with suitable properties for end use applications. Typical examples may include corrosion inhibitors, emulsifiers, fragrances, dyes, preservatives, thickening agents, hydrotrope agents, or combinations thereof, and the like.

The biocidal compositions having a QAE compound and a hydrogen peroxide source, as previously mentioned, may be used in numerous and diverse applications, as previously mentioned. For example, in one embodiment, the biocidal composition may be used to sanitize or disinfect hard, non-porous surfaces. Furthermore, such a composition, as described, is well suited for disinfecting or sanitizing flooring materials, countertops, ceramic surfaces, metal surfaces, glass surfaces, stone surfaces, and the like. For example, the compositions may be used to clean the surfaces, destroy microorganisms on the surface and/or prevent growth of microorganisms on the surface.

Another example includes the use of such a biocidal composition in the food service industry, to disinfect and sanitize food processing equipment and other food processing surfaces or to wash produce, such as vegetables. Such a composition may also be used in the healthcare industry to disinfect surfaces, facility, equipment and hospital instruments and equipment, and/or disinfect utensils.

Additionally, a method of treating recirculating water using an effective amount of the water treatment composition, as described wherein the composition is contacted for an amount of time sufficient to kill microbes present in the water.

Typically water treatment applications, include but are not limited to, water sources of industrial process water systems, process water applications, process waters, utility waters, water used in manufacturing, water used in industrial services, aqueous liquid streams, liquid stream, cooling towers, recirculating water systems, recreational water, recycled water, industrial water, and/or any other suitable or desirable fresh or sea water source that is frequently subject to excessive plant growth, including algae, cyanobacteria, fungi, mold, mildew, and the like.

Suitable examples of such bodies of water include, but are not limited to, swimming pools, spas, ponds, lakes, streams, canals, and any body of water (fresh or salt water source), that is frequently subject to excessive plant growth, including algae, cyanobacteria, and the like.

For example, a method of treating recirculating water using an effective amount of the water treatment composition, according to the present invention is described, wherein the composition is contacted for an amount of time sufficient to kill microbes present in the water; and wherein the water is a swimming pool, pond, lake, stream, canal.

Another aspect of the invention describes a water treatment composition comprising (a) an effective amount of one or more of a quaternary ammonium etidronate compound or derivative thereof as described, (b) a water treating biocidal agent, (c) a hydrogen peroxide source and (d) water.

The present invention provides the use of one or more QAE compounds in combination with a hydrogen peroxide source and/or other acids for water treatment applications, comprising cooling towers and recirculating water systems. This embodiment provides a method of disinfecting a surface of microorganisms by contacting the surface with the disinfecting composition for an amount of time effective to kill a majority of the microbes located on the surface. Such microorganisms include, but not limited to, gram positive bacteria, gram negative bacteria, viruses, fungi, mildew, mold and combinations thereof.

Additionally the disclosure also provides a method of using the composition of QAE or derivative thereof, having the Formula I-V, with a hydrogen peroxide source or other biocidal agent, as another water treatment or biocidal composition. For example, one embodiment describes a composition having a quaternary ammonium etidronate compound and a hydrogen peroxide source together, which may be used to kill or to inhibit the growth of microorganisms such as gram positive or gram negative bacteria, viruses, fungi, mildew, mold or combinations thereof, for water applications.

The combination of QAE compound with the hydrogen peroxide source may enhance the biocidal efficacy in comparison to a hydrogen peroxide source used along. Such compositions have shown improved microbial efficacy against a variety of microorganisms that are potentially harmful or capable of causing disease, such as gram positive and gram negative bacteria, viruses, fungi, mildew, and mold. Examples of such microorganisms include, but are not limited to, *Staphylococcus, Pseudomonas*, hepatitis, rotavirus, rhinovirus, or *Mycobacterium terrae*. In an aspect, the compositions has improved microbial efficacy against *S. aureus, E. coli, Candida albicans, Aspergillus niger, P. aeruginosa, B. mycoides, A. niger*, and *C. pyrenoidosa* especially *Mycobacterium terrae*.

The following examples illustrate the invention without limitation. All parts and percentages are given by weight unless otherwise indicated.

It will be understood that each of the elements described in the examples below, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

Example 1

Typically a 2:1 ratio solution of QAE was formed by reacting about 2 molar ratio of quaternary ammonium cation and about 1 molar ratio of etidronic acid. The quaternary ammonium cation used was 81.49 g of didecyldimethylammonium carbonate (50% active), 18.5 g of etidronic acid (HEDP, 60%), along with the addition of water (12.05 mL), and an anti-foaming agent (0.1%, polydimethylsiloxane). The reactants were mixed for about 1 to about 5 hr., at a temperature between 25 to about 90° C.; then cooled, at relative room temperature, having a final pH of 4.90. The percent yield of quaternary ammonium cation was 31.9%.

Example 2

Typically a 1:1 ratio of QAE was formed by reacting about 1 molar ratio of quaternary ammonium cation and about 1 molar ratio of etidronic acid. The quaternary ammonium cation used was 40.04 g of didecyldimethylammonium carbonate (50% active), 18.07 g of HEDP (60%), along with water (4 mL), 4.22 g of NaOH (50%), and an anti-foaming agent (0.05%, polydimethylsiloxane). The reactants were mixed for about 1 to about 5 hr., at a temperature between 25 to about 90° C.; then cooled, at relative room temperature, having a final pH of 3.01. The percent yield of quaternary ammonium cation was 27.37%, through the addition of a base (NaOH).

Example 3

Typically a 4:1 ratio of QAE was formed by reacting about 4 molar ratio of quaternary ammonium cation and 1 molar ratio of etidronic acid. The quaternary ammonium cation used was 50.02 g of didecyldimethylammonium carbonate (50% active), 5.86 g of HEDP (60%), water (4.01 mL), and an anti-foaming agent (0.05% polydimethylsiloxane) were mixed to yield a composition having a pH of 8.34, yielding 38.21% quaternary ammonium cation. The reactants were mixed for about 1 to about 5 hr., at a temperature between 25 to about 90° C. then cooled, at relative room temperature.

Example 4

A biocidal composition containing a hydrogen peroxide/water mixture and varied concentrations of QAE may be used for the treatment of cooling towers or recirculating water systems. The formulation consists of a QAE compound formed as shown in examples 1-3, typically having about 5% to about 35% quaternary ammonium etidronate or derivative thereof, about 0.1 to about 25% of a hydrogen peroxide source (50% active), and water. The percentage weight of each active is based on the weight percent of the total composition.

Example 5

A water treatment composition containing hydrogen peroxide/water mixture and typically a 2:1 ratio of QAE may be used for the treatment of cooling towers and recirculating water systems. The biocidal composition consists of QAE formed as shown in examples 1, typically having about 25% quaternary ammonium etidronate or derivative thereof, about 15% hydrogen peroxide source/water mixture (50% active), about 0.1% to about 10% weight of a carboxylic acid and water. The percentage weight of each active is based on the weight percent of the total composition.

The composition as described in example 1 was tested biocidal activity against various microorganisms such as *Pseudomonas aeruginosa, B. mycoides, A. niger*, and *C. pyrenoidosa*. The results showed efficacy against various gram positive and gram negative microorganisms with 7.81 ppm against *P. aeruginosa*, <0.98 against *B. mycoides*, ppm against *A. niger* and <0.98 ppm against *C. pyrenoidosa*. The test pH for the bacteria was about 7.2, about 5.6 for fungi, and about 7.4 for the algae.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A quaternary ammonium etidronate compound, comprising a quaternary ammonium cation and an etidronate anion, having the Formula I,

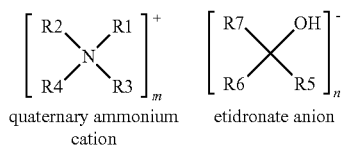

quaternary ammonium cation    etidronate anion wherein in the quaternary ammonium cation in the Formula I, R1 or R2, is a H or a substituted or unsubstituted straight chain or branched $C_1$-$C_8$ alkyl, aryl, alkylaryl/arylalkyl, cycloalkyl, (aromatic or non-aromatic) heterocyclyl, or alkoxy;

R3 or R4 is a substituted or unsubstituted straight chain or branched $C_6$-$C_{30}$ alkyl, aryl, alkylaryl/arylalkyl, cycloalkyl, (aromatic or non-aromatic) heterocyclyl, alkenyl, phenyl, alkyl-substituted phenyl, benzyl, naphthylmethyl, or ethylbenzyl group;

wherein two or more of R1, R2, R3 and R4 may together with a nitrogen atom form a substituted or unsubstituted heterocyclic ring; and wherein the total number of carbon atoms in the groups R1, R2, R3 and R4 must be at least 12;

wherein the quaternary ammonium cation, comprises a $C_8$-$C_{30}$ dialkyldimethyl ammonium, $C_8$-$C_{30}$ dialkylmethylpoly(oxyethyl) ammonium, $C_8$-$C_{30}$ alkylbenzyldimethyl ammonium, $C_8$-$C_{30}$ alkyltrimethylammonium, $C_8$-$C_{30}$ dialkyldihydroxyethyl ammonium, $C_8$-$C_{30}$ dialkylmethylhydroxyethyl ammonium, or $C_8$-$C_{30}$ alkylmethyldihydroxyethyl ammonium;

wherein the etidronate anion, having the Formula I, is an etidronic salt wherein R5 and R6 is $PO_3^{2-}$ or $PO_3X_y$; wherein each X is a H, M, H$^-$, HM, M$^-$ or M$^+$; wherein y is 0-2; and M is lithium, sodium, potassium or any combinations thereof, and wherein R7 group is a H or a substituted or unsubstituted straight chain or branched $C_1$-$C_8$ alkyl;

wherein m is 1-4 and n is 1; and wherein the quaternary ammonium etidronate compound does not comprise a chloride ion.

2. The compound of claim 1, wherein R1, R2, R3 or R4 when substituted comprises substituent groups selected from one or more of a F, Br, I, Cl, —OR', —NR'R", —CF$_3$, —CN, —NO$_2$, —C$_2$R', —SR', —N$_3$, —C(=O)NR'R", —NR'C(O)R", —O(CR'R")rC(=O)R', —O(CR'R")rNR'C(O)R', —(CR'R")rNR"SO$_2$R', —OC(O)NR'R", —NR'C(O)OR", —SO$_2$R', —SO$_2$NR'R", —NR'SO$_2$R"; or combinations thereof, wherein R' and R" are individually hydrogen, $C_1$-$C_8$ alkyl, cycloalkyl, heterocyclyl, aryl, or arylalkyl, and is an integer from 1 to 6, or R' and R" together form a cyclic functionality.

3. The compound of claim 1, wherein the etidronate anion, having the group R5 is a PO32-, PO3H2, PO3M2, PO3HM, PO3H— or PO3M- and the group R6 is a PO32-, PO3H2, PO3M2, PO3HM, PO3H— or PO3M-.

4. The compound of claim 1, wherein the quaternary ammonium etidronate is one having the Formula II, III, IV, V or combinations thereof, and wherein R1-R4 are as defined according to claim 1.

5. A method for the preparation of a quaternary ammonium etidronate compound, said method comprising reacting a quaternary ammonium compound with an etidronate anion, as shown in Schematic A,

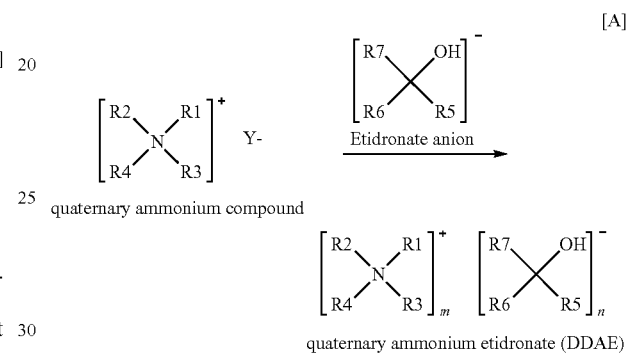

quaternary ammonium compound quaternary ammonium etidronate (DDAE)

wherein in the quaternary ammonium compound R1 or R2, is a H or a substituted or unsubstituted straight chain or branched $C_1$-$C_8$ alkyl, aryl, alkylaryl/arylalkyl, cycloalkyl, (aromatic or non-aromatic) heterocyclyl, or alkoxy;

R3 or R4 is a substituted or unsubstituted straight chain or branched $C_6$-$C_{30}$ alkyl, aryl, alkylaryl/arylalkyl, cycloalkyl, (aromatic or non-aromatic) heterocyclyl, alkenyl, phenyl, alkyl-substituted phenyl, benzyl, naphthylmethyl, or ethylbenzyl group;

wherein two or more of R1, R2, R3 or R4 may together with a nitrogen atom form a substituted or unsubstituted heterocyclic ring; and wherein the total number of carbon atoms in the groups R1, R2, R3 or R4 must be at least 12;

wherein the etidronate anion, having the Formula I, is an etidronic salt wherein R5 and R6 is $PO_3^{2-}$ or $PO_3X_y$; wherein each X is a H, M, H$^-$, HM, M$^-$ or M$^+$; wherein y is 0-2; and M is lithium, sodium, potassium or any combinations thereof, and wherein R7 group is a H or a substituted or unsubstituted straight chain or branched $C_1$-$C_8$ alkyl;

wherein the etidronate anion comprises an ion of 1-hydroxyethane 1,1-diphosphonic acid (HEDP or etidronic acid), sodium etidronate, disodium etidronate (1-Hydroxyethanediphosphonic acid, sodium salt), dilithium etidronate, dipotassium etidronate, trisodium etidronate, tetrasodium etidronate, tetrapotassium etidronate or combinations thereof;

wherein Y$^-$ is an anion, and wherein said quaternary ammonium compound reactant or etidronate anion is present at variable ratios.

6. The method as defined in claim 5, wherein the weight ratio of the quaternary ammonium cation to the etidronate anion is from about 1:1 to about 4:1.

7. The method as defined in claim 5, wherein the quaternary ammonium compound reactant is a quaternary salt; wherein a Y⁻ anion comprises carbonates, bicarbonates, halides, phosphates, sulfates, bisulfates, acetates, nitrates, hydroxides, salicylates, bentonites, molybdates, formates, borates, sulfonates, phosphites, hypophosphite, or combinations thereof.

8. The method as defined in claim 5, wherein the quaternary ammonium etidronate is formed by reacting a quaternary ammonium carbonate, bicarbonate or hydroxide with etidronic acid, as shown in Schematic B, 15. The water treatment composition as defined in claim 13, wherein the water treating biocidal agent comprises a halogen releasing agent; a peroxy compound; a hydrogen peroxide source; an isothiazolone, derivatives or a mixture of isothiazolones; an amine, or combinations thereof.

16. The water treatment composition as defined in claim 15, wherein the halogen releasing agent comprises a chlorinated isocyanuric acids or salts thereof, halogenated hydantoins, hypochlorous acid, hypochlorite salts or salts thereof, chlorine gas, chlorine dioxide, hypobromite salts, hypobromous acid or combinations thereof.

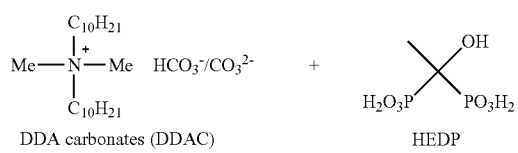

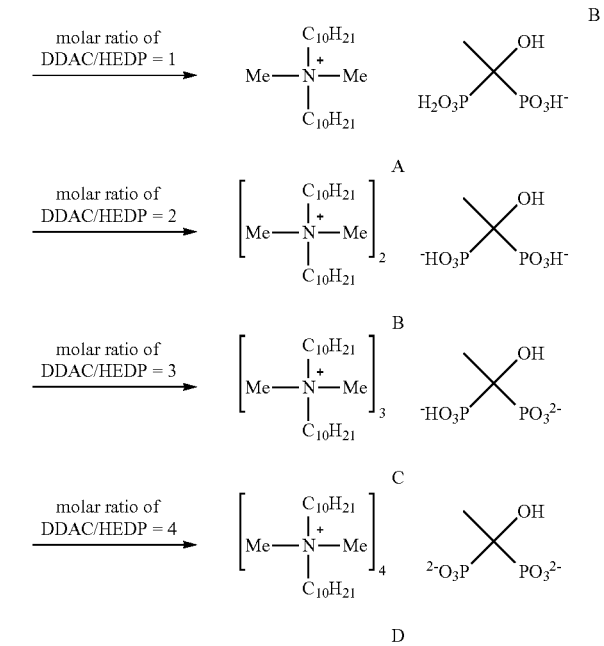

wherein said quaternary ammonium compound reactant to etidronic acid is present at variable ratios of about 1:1 to about 4:1.

9. The method as defined in claim 8, wherein the reaction takes places in the presence of an aqueous solvent comprising of water, aqueous alcohols, ammonia water, acid solutions, salt solutions, water-miscible organic solvents, glycols, or combinations thereof.

10. The method as defined in claim 8, wherein the reaction takes places in the presence of an optional antifoaming agent; wherein the antifoaming agent comprises polydimethylsiloxaneanti-foam.

11. The method as defined in claim 8, wherein the reaction takes places in the presence of an optional base; wherein the base comprises a strong or weak base.

12. A method of treating recirculating water using one or more compounds as defined according to claim 1, wherein the compound is contacted for an amount of time sufficient to kill microbes present in the water.

13. A water treatment composition comprising one or more of a quaternary ammonium etidronate compound or derivative thereof, as defined according to claim 1, and a water treating biocidal agent.

14. The water treatment composition according to claim 13, wherein the quaternary ammonium compound or derivative thereof is present from about 5 w/w % to about 35 w/w % of the total composition; and the water treating biocidal agent is present from about 0.1 w/w % to 25 w/w % of the total composition.

17. The water treatment composition, as defined in claim 13, further comprising an acid, a carboxylic acid or mineral acid, wherein the total concentration of the acid is from about 0.1 w/w % to 10 w/w % of the total composition.

18. The water treatment composition as defined in claim 13, further comprising a stabilizer selected from an organic and inorganic sequestering agent, wherein the stabilizer is present from about 0.01 w/w % to about 5 w/w % of the total composition.

19. The water treatment composition, according to claim 13, further comprising a second biocidal agent, wherein the second biocidal agent is present from about 0.1 w/w % to about 25 w/w % of the total composition.

20. A water treatment composition comprising (a) an effective amount of one or more of a quaternary ammonium etidronate compound or derivative thereof, as defined according to claim 1, (b) a water treating biocidal agent, (c) a hydrogen peroxide source and (d) water.

21. A method of treating a body of water, wherein the water is a swimming pool, pond, lake, stream, canal; said method comprises adding the composition according to claim 20 to the water.

22. A water treatment, cosmetic, hygiene, personal care, paint, coating, wood treatment, agrochemical, antimicrobial, biocidal or disinfectant composition comprising one or more compounds according to claim 1.

23. The compound of claim 1, wherein m is 4.
24. The compound of claim 5, wherein Y– is a carbonate anion or a bicarbonate anion.

* * * * *